United States Patent [19]

Sabourin

[11] Patent Number: 5,457,211

[45] Date of Patent: Oct. 10, 1995

[54] HYDROXYALKYL-SUBSTITUTED CYCLIC UREA-SUBSTITUTED AMINES

[75] Inventor: Edward T. Sabourin, Novato, Calif.

[73] Assignee: Chevron U.S.A. Inc., San Francisco, Calif.

[21] Appl. No.: 194,618

[22] Filed: Feb. 10, 1994

Related U.S. Application Data

[63] Continuation of Ser. No. 833,544, Feb. 10, 1992, abandoned.

[51] Int. Cl.[6] .................... C07D 233/36; C07D 239/10
[52] U.S. Cl. ......................... 548/323.5; 544/316
[58] Field of Search .................... 544/316; 548/323.5

[56] References Cited

U.S. PATENT DOCUMENTS

| | | | |
|---|---|---|---|
| 3,380,909 | 4/1968 | Lee | 208/48 |
| 3,438,757 | 4/1969 | Honnen et al. | 44/58 |
| 3,491,025 | 1/1970 | Lee | 252/49.6 |
| 3,509,085 | 4/1970 | Sckmakas | 548/323.5 |
| 3,556,995 | 1/1971 | Lee et al. | 252/39 |
| 3,565,804 | 2/1971 | Honnen et al. | 252/50 |
| 3,574,576 | 4/1971 | Honnen et al. | 44/72 |
| 3,794,586 | 2/1974 | Kimura et al. | 252/51.5 |
| 3,898,056 | 8/1975 | Honnen | 44/58 |
| 3,960,515 | 6/1976 | Honnen | 44/58 |
| 3,965,084 | 6/1976 | Schiff | 260/96.5 R |
| 4,108,613 | 8/1978 | Frost, Jr. | 44/62 |
| 4,123,232 | 10/1978 | Frost, Jr. | 44/72 |
| 4,152,499 | 5/1979 | Boerzel et al. | 526/52.4 |
| 4,191,537 | 3/1980 | Lewis et al. | 44/71 |
| 4,319,032 | 3/1982 | Sandri et al. | 548/323.5 |
| 4,605,808 | 8/1986 | Samson | 585/525 |
| 4,846,848 | 7/1989 | Miles et al. | 44/62 |

*Primary Examiner*—Jacqueline Haley
*Attorney, Agent, or Firm*—W. K. Turner; E. A. Schaal

[57] ABSTRACT

A fuel composition comprising a major amount of hydrocarbons boiling in the gasoline or diesel range and an effective detergent amount of a hydroxyalkyl-substituted, five- or six-membered cyclic urea-substituted monoamine or diamine which is the reaction product of:

(a) a polyolefin epoxide derived from a branched-chain polyolefin having an average molecular weight of about 400 to 5000;

(b) a polyamine having from 3 to 4 amine nitrogen atoms and from 4 to 9 carbon atoms; and thereafter (c) urea.

5 Claims, No Drawings

HYDROXYALKYL-SUBSTITUTED CYCLIC UREA-SUBSTITUTED AMINES

This is a continuation of application Ser. No. 07/833,544, filed Feb. 10, 1992, abandoned.

BACKGROUND OF THE INVENTION

1. Field of the Invention

In recent years, numerous fuel detergents or "deposit control" additives have been developed. These materials when added to hydrocarbon fuels employed in internal combustion engines effectively reduce deposit formation which ordinarily occurs in carburetor ports, throttle bodies, ventures, intake ports and intake valves. The reduction of these deposit levels has resulted in increased engine efficiency and a reduction in the level of hydrocarbon and carbon monoxide emissions.

Furthermore, as engines age, they suffer from a need for a higher octane base gasoline. It is desirable to produce an additive for gasoline which is not only an effective deposit control additive but also has a low ORI (octane requirement increase) property.

Due to the synthetic procedures employed in the manufacture of many of these deposit control additives, such additives often contain small amounts of residual chlorine. In the past, the amount of residual chlorine contained in these additives was usually considered insignificant in comparison to other sources of chlorine typically present in leaded fuels. However, with the advent of non-leaded gasolines, it has become possible to remove many of these other chlorine sources found in fuels. The removal of chlorine from fuels is particularly advantageous, since the combustion process may convert the chlorine into environmentally undesirable emission products.

It is, therefore, highly desirable to provide fuel compositions which contain deposit control additives which effectively control deposits in intake systems (carburetor, valves, etc.) of engines operated with fuels containing them, but do not contribute to chlorine-containing emissions, and, most preferably have a low ORI effect.

2. Description of the Prior Art

U.S. Patent Nos. 3,438,757 and 3,574,576 to Honnen et al. disclose high molecular weight branched-chain aliphatic hydrocarbon N-substituted amines and alkylene polyamines which are useful as detergents and dispersants in hydrocarbonaceous liquid fuels for internal combustion engines. These hydrocarbyl amines and polyamines have molecular weights in the range of about 425 to 10,000, and more usually in the range of about 450 to 5000. Such high molecular weight hydrocarbyl polyamines are also taught to be useful as lubricating oil additives in U.S. Pat. No. 3,565,804 to Honnen et al. U.S. Pat. Nos. 3,898,056 and 3,960,515 to Honnen et al. disclose a mixture of high and low molecular weight hydrocarbyl amines used as detergents and dispersants at low concentrations in fuels. The high molecular weight hydrocarbyl amine contains at least one hydrocarbyl group having a molecular weight from about 1900 to 5000 and the low molecular weight hydrocarbyl amine contains at least one hydrocarbyl group having a molecular weight from about 300 to 600. The weight ratio of low molecular weight amine to high molecular weight amine in the mixture is maintained between about 0.5:1 and 5:1.

U.S. Pat. Nos. 4,123,232 and 4,108,613 to Frost disclose pour point depressants for hydrocarbonaceous fuels which are the reaction products of an epoxidized alpha olefin containing from 14 to 30 carbon atoms and a nitrogen-containing compound selected from an amine, a polyamine and a hydroxyalkyl amine.

U.S. Pat. No. 3,794,586 to Kimura et al. discloses lubricating oil compositions containing a detergent and antioxidant additive which is a hydroxyalkyl-substituted polyamine prepared by reacting a polyolefin epoxide derived from branched-chain olefins having an average molecular weight of 140 to 3000 with a polyamine selected from alkylene diamines, cycloalkylene diamines, aralkylene diamines, polyalkylene polyamines and aromatic diamines, at a temperature of 15° C. to 180° C.

U.S. Pat. No. 3,380,909 to Lee describes the reaction:

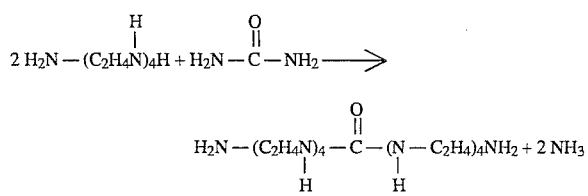

This polyaminourea is reacted with an alkylsuccinimide to make an anti-foulant additive.

The same or similar chemistry is shown in U.S. Pat. Nos. 3,491,025 and 3,556,995 also to Lee and the products are taught as useful as detergents-dispersants in lube oils.

U.S. Pat. No. 3,965,084 to Sidney Schiff entitled "Ashless Dispersant Products and Process" relates to improved additives for lubricants and motor fuels which are prepared by reacting a petroleum sulfonic acid with an adduct formed from an amine and either urea or thiourea (see Col. 1, lines 7 et seq.). A wide variety of amines can be used to form the adduct (see Col. 5, lines 14 to 36), but there is no hydroxyl group on Schiff's adduct. The preferred mole ratio of amine to urea or thiourea is 1.5:1 to 2.25:1 (see Col. 5, lines 38–41). Runs 2 and 3, summarized in Table 1 in Col. 7, show the reaction of tetraethylene pentamine (TEPA) (which is outside the definition of useful amines for the subject invention) with urea and footnote "a" of Table 1 shows that Schiff expected the product to be a dimer. There is no teaching in Schiff that a cyclic urea would be formed. One with ordinary skill in the art would expect (from the teachings of Schiff in Table 1 and in the preferred ratios of amine to urea) the formation of a dimer-like product.

SUMMARY OF THE INVENTION

A fuel composition is provided which contains a deposit control additive which aids the composition in maintaining cleanliness of engine intake systems; advantageously contains no residual chlorine; and has a low ORI factor. Accordingly, the novel fuel compositions of this invention comprise a major amount of hydrocarbons boiling in the gasoline or diesel range and an effective detergent amount of a hydroxyalkyl-substituted five- or six-membered cyclic urea-substituted monoamine or diamine. These substituted monoamines or diamines are the reaction product of (a) a polyolefin epoxide derived from a branched-chain polyolefin having an average molecular weight of about 400 to 5000; (b) a polyamine having from 3 to about 4 amine nitrogen atoms and from 4 to 9 carbon atoms; and (c) urea. The cyclic urea-substituted monoamine or diamines are also new compositions per se.

The present invention further provides a fuel concentrate comprising an inert stable oleophilic organic solvent boiling in the range of from about 150° F. to 400° F. and from 10 to 50 weight percent of the hydroxyalkyl-substituted five- or six-membered cyclic urea-substituted monoamine or diamine reaction product described above.

DETAILED DESCRIPTION OF THE INVENTION

The hydroxyalkyl-substituted five- or six-membered cyclic urea-substituted monoamine or diamine additive employed in the fuel composition of the present invention comprises the reaction product of (a) a polyolefin epoxide derived from a branched-chain polyolefin having an average molecular weight of about 400 to 5000; (b) a polyamine having from 3 to 4 amine nitrogen atoms and from 4 to about 9 carbon atoms; and (c) urea. The polyamine component of this reaction product is selected to provide deposit control activity with low octane requirement increase.

The Polyolefin Epoxide Component

The polyolefin epoxide component used to prepare the presently employed hydroxyalkyl-substituted portion of the monoamine or diamine reaction product is obtained by oxidizing a polyolefin with an oxidizing agent to give an alkylene oxide, or epoxide, in which the oxirane ring is derived from oxidation of the double bond in the polyolefin.

The polyolefin starting material used in the preparation of the polyolefin epoxide is a high molecular weight branched-chain polyolefin having an average molecular weight of about 400 to 5000, and preferably from about 900 to 2500.

Such high molecular weight polyolefins are generally mixtures of molecules having different molecular weights and can have at least one branch per 6 carbon atoms along the chain, preferably at least one branch per 4 carbon atoms along the chain, and particularly preferred that there be about one branch per 2 carbon atoms along the chain. These branched-chain olefins may conveniently comprise polyolefins prepared by the polymerization of olefins of from 2 to 6 carbon atoms, and preferably from olefins of from 3 to 4 carbon atoms, and more preferably from propylene or isobutylene. When ethylene is employed, it must be copolymerized with another olefin so as to provide a branched-chain polyolefin. The addition-polymerizable olefins employed are normally 1-olefins. The branch may be of from 1 to 4 carbon atoms, more usually of from 1 to 2 carbon atoms, and preferably methyl.

In general, any high molecular weight branched-chain polyolefin isomer whose epoxide is capable of reacting with a polyamine is suitable for use in preparing the presently employed fuel additives. However, sterically hindered epoxides, such as tetra-alkyl substituted epoxides, are generally slower to react.

Particularly preferred polyolefins are those containing an alkylvinylidene isomer present in an amount at least about 20%, and preferably at least 50%, of the total polyolefin composition. The preferred alkylvinylidene isomers include methylvinylidene and ethylvinylidene, more preferably the methylvinylidene isomer.

The especially preferred high molecular weight polyolefins used to prepare the instant polyolefin epoxides are polyisobutylenes which comprise at least about 20% of the more reactive methylvinylidene isomer, preferably at least 50% and more preferably at least 70%. Suitable polyisobutylenes include those prepared using $BF_3$ catalysts. The preparation of such polyisobutylenes in which the methylvinylidene isomer comprises a high percentage of the total composition is described in U.S. Pat. Nos. 4,152,499 and 4,605,808.

Examples of suitable polyisobutylenes having a high alkylvinylidene content include (1) Ultravis 30™, a polyisobutylene having a molecular weight of about 1,300 and a methylvinylidene content of about 76%, and (2) Ultravis 10™, a polyisobuyltene having a molecular weight of about 950 and a methylvinylidene content of about 76%, both available from British Petroleum.

As noted above, the polyolefin is oxidized with a suitable oxidizing agent to provide an alkylene oxide, or polyolefin epoxide, in which the oxirane ring is formed from oxidation of the polyolefin double bond.

The oxidizing agent employed may be any of the well known conventional oxidizing agents used to oxidize double bonds. Suitable oxidizing agents include hydrogen peroxide, peracetic acid, perbenzoic acid, performic acid, monoperphthalic acid, percamphoric acid, persuccinic acid and pertrifluoroacetic acid. The preferred oxidizing agent is peracetic acid.

When peracetic acid is used as the oxidizing agent, generally a 40% peracetic acid solution and about a 5% equivalent of sodium acetate (as compared to the peracetic acid) is added to the polyolefin in a molar ratio of peracid to olefin in the range of about 1.5:1 to 1:1, preferably about 1.2:1. The mixture is gradually allowed to react at a temperature in the range of about 20° C. to 90° C.

The resulting polyolefin epoxide, which is isolated by conventional techniques, is generally a liquid or semi-solid resin at room temperature, depending on the type and molecular weight of olefin employed.

Amine Component

The amine component used to prepare the presently employed hydroxylalkyl-substituted mono and diamine reaction products are derived from a polyamine having from 3 to 4 amine nitrogen atoms and from 4 to about 9 carbon atoms. The polyamine is reacted with a polyolefin epoxide to produce the hydroxyalkyl-substituted polyamine portion of the fuel additive finding use within the scope of the present invention. The polyamine provides a reaction product; i.e., after reaction of the polyamine with urea, with at least one basic nitrogen atom per product molecule; i.e., a nitrogen atom titratable by a strong acid.

The preferred polyamines finding use within the scope of the present invention are those having the formula:

where X and Y can be the same or different and are selected from the group consisting of $-CH_2CH_2-$; $-CH_2CH_2CH_2-$; and

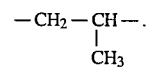

Examples of suitable polyamines include but are not limited to:

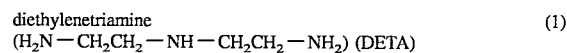

-continued di(1,3-propylene)triamine (2)
(H₂N—CH₂CH₂CH₂—NH—CH₂CH₂CH₂—NH₂)

di(1,2-propylene)triamine (3)
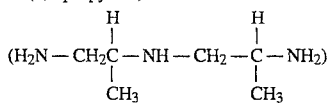

triethylenetetraamine (4)
[H₂N—CH₂CH₂—NH—CH₂CH₂—NH—CH₂CH₂—NH₂]
(TETA)

tri(1,3-propylene)tetraamine (5)
[H₂N(CH₂)₃NH(CH₂)₃NH(CH₂)₃NH₂] (TPTA)

The third component used in the preparation of the new substituted polyamines of this invention is urea

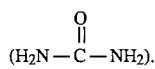

As will be described more fully below, the hydroxyalkyl-substituted five- or six-membered cyclic urea-substituted mono and diamines are prepared by reacting the described polyolefin epoxide with the defined polyamine and this product is then reacted with urea to form the new cyclic urea compositions of this invention.

The preferred new cyclic ureas are selected from the monoamine and diamines having the formula:

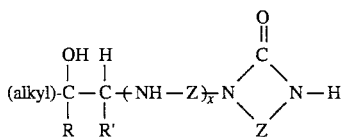

where alkyl is a branched-chain polyolefin having an average molecular weight from 400 to 5000, preferably from 900 to about 2,500 and wherein the olefin has from 2 to 6 carbon atoms, preferably 3 to 4 carbon atoms and more preferably is propylene or isobutylene;

R and R' can be the same or different and are selected from hydrogen or a lower alkyl group having 1 to 4 carbon atoms;

x can be the integer 1 or 2; and

Z is the same or different and is selected from the group consisting of —CH₂CH₂—; —CH₂CH₂CH₂—; and

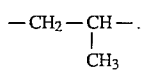

The above formula is an hydroxyalkyl-substituted five- or six-membered cyclic urea-substituted monoamine when x is 1 or a substituted diamine when x is 2.

Surprisingly, the reaction of the hydroxyalkyl-substituted mono or diamine with urea results in the production of a cyclic urea plus two moles of free ammonia. From the prior art to Lee and Schiff, discussed above, it was expected that a linear dimer of urea would form.

These new cyclic ethers were then found to have surprisingly good detergent and ORI properties as will be shown below.

Preparation Of The Hydroxyalkyl-Substituted Five-
Or Six-Membered Cyclic Urea-Substituted
Monoamine Or Diamine Reaction Product As noted above, the fuel additive finding use in the present invention is a hydroxyalkyl-substituted five- or six-membered cyclic urea-substituted monoamine or diamine which is the reaction product of (a) a polyolefin epoxide derived from a branched-chain polyolefin having an average molecular weight of about 400 to 5000; (b) a polyamine having from 3 to 4 amine nitrogen atoms and from 4 to 9 carbon atoms; and (c) urea.

The reaction of the polyolefin epoxide and the polyamine is generally carried out either neat or with a solvent at a temperature in the range of about 100° C. to 250° C. and preferably from about 180° C. to about 220° C. The reaction usually is conducted in the absence of oxygen, and may be carried out in the presence or absence of a catalyst. The desired product may be obtained by water wash and stripping, usually by aid of vacuum, of any residual solvent.

The mole ratio of basic amine nitrogen to polyolefin epoxide will generally be in the range of about 3 to 50 moles of basic amine nitrogen per mole of epoxide, and more usually about 5 to 20 moles of basic amine nitrogen per mole of epoxide. The mole ratio will depend upon the particular amine and the desired ratio of epoxide to amine. Since suppression of polysubstitution of the polyamine is usually desired, large mole excesses of the polyamine will generally be used.

The reaction of polyolefin epoxide and polyamine may be conducted either in the presence or absence of a catalyst, thermal reaction being preferred. When employed, suitable catalysts include Lewis acids, such as aluminum trichloride, boron trifluoride, titanium tetrachloride, ferric chloride, and the like traces of which can be removed after reactions by washing or the like. Other useful catalysts include solid catalysts containing both Bronsted and Lewis acid sites, such as alumina, silica, silica-alumina, and the like.

The reaction may also be carried out with or without the presence of a reaction solvent. A reaction solvent is generally employed whenever necessary to reduce the viscosity of the reaction product. These solvents should be stable and inert to the reactants and reaction product.

Preferred solvents include aliphatic or aromatic hydrocarbons or aliphatic alcohols.

Depending on the temperature of the reaction, the particular polyolefin epoxide used, the mole ratios and the particular polyamine, as well as the presence or absence of a catalyst, the reaction time may vary from less than 1 hour to about 72 hours.

After the reaction has been carried out for a sufficient length of time, the reaction mixture may be subjected to extraction with a hydrocarbon-water or hydrocarbon-alcohol-water medium to free the product from any low-molecular weight amine salts which have formed and any unreacted polyamines. The product may then be isolated by evaporation of the solvent.

In most instances, the additive compositions used in this invention are not a pure single product, but rather a mixture of compounds. Usually, the range of molecular weights will be relatively narrow. Similarly, for the more complicated polyamines containing 4 nitrogens, the compositions will be a mixture of amines having one major product and minor amounts of analogous compounds relatively close in composition to the dominant compound.

The hydroxyalkyl-substituted polyamine is then reacted with urea and can be represented as follows:

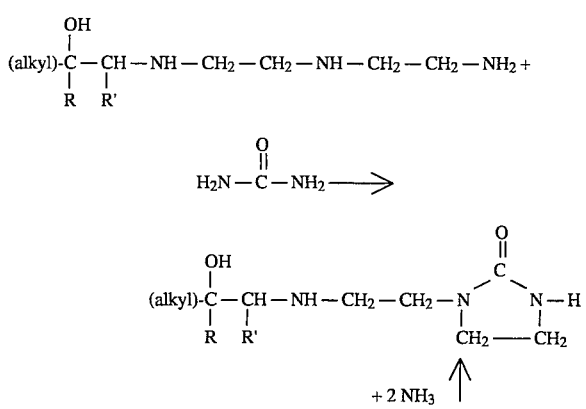

where alkyl and R and R' are as defined above.

The reaction of the hydroxyalkyl-substituted polyamine with the urea is usually carried out either neat or with a solvent at a temperature in the range of 75° C. to 250° C., preferably 140° C. to 180° C. The reaction is usually conducted in the absence of oxygen and may be carried out in the presence or absence of a catalyst. The desired product is recovered by sparging with nitrogen or applying a vacuum to remove traces of ammonia. Alternatively a water wash could be used.

The mole ratio of the urea to the hydroxyalkyl-substituted polyamine is usually about 1:1, but higher or lower ratios can be used. The preferred ratios are 0.8:1 to 1.2:1. The reaction time is usually from 0.5 to 20 hours and more usually from 1 to 8 hours. These reaction variables are not critical and are well within the skill of those in the art.

Ammonia is a gaseous by-product and is usually removed during reaction to drive the reaction to the desired product. The ammonia is removed and treated in known ways.

The reaction solvents, if employed, should be stable and inert to the reactants and products. Preferred solvents include aliphatic or aromatic hydrocarbons or aliphatic alcohols.

Fuel Compositions

The hydroxyalkyl-substituted, five- or six-membered cyclic urea-substituted monoamine or diamine is useful as an additive for a hydrocarbon distillate fuel. The proper concentration of additive necessary in order to achieve the desired detergency and dispersancy varies depending upon the type of fuel employed, the presence of other detergents, dispersants and other additives, etc. Generally, however, from 30 to 2000 weight ppm, preferably from 100 to 500 ppm of the substituted monoamine or diamine additives of the invention per part of base fuel is needed to achieve the best results. When other detergents are present, a lesser amount of additive may be used. For performance as a carburetor detergent only, lower concentrations, for example 30 to 70 ppm may be preferred.

The deposit control additive may be formulated as a concentrate, using an inert stable oleophilic (i.e., dissolves in gasoline) organic solvent boiling in the range of about 150° F. to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the detergent-dispersant additive. In the concentrate, the amount of the additive will be ordinarily at least 10% by weight and generally not exceed 70% by weight, preferably 10–50 weight percent and most preferably from 10 to 25 weight percent.

In gasoline fuels, other fuel additives may also be included such as antiknock agents, e.g., methylcyclopentadienyl manganese tricarbonyl or other dispersants or detergents such as various substituted succinimides, amines, etc. preferably halogen free. Additionally, antioxidants, metal deactivators and demulsifiers may be present.

A particularly useful additive is a fuel-soluble nonvolatile carrier oil. The carrier fluid employed in this invention is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, synthetic polyoxyalkylene derived oils, and the like, as described, for example, in U.S. Pat. No. 4,191,537 to Lewis. These carrier fluids are believed to act as a carrier for the dispersant and detergent and to assist in removing and retarding deposits.

The carrier fluid employed in the instant invention must also be capable of forming a homogeneous mixture with the other components of the present fuel additive composition. Examples of suitable carrier fluids include Chevron Neutral Oil 500R and Chevron Neutral Oil 600P, available from Chevron U.S.A. Inc., San Francisco, Calif.

Exemplary carrier oils include nonvolatile poly(oxyalkylene) compounds; other synthetic lubricants, i.e., polyalphaolefins or a lubricating mineral oil. The carrier oils are employed in amounts from 100 to 5000 ppm by weight of the fuel, preferably from 500 to 3000 ppm of the fuel. The polyalphaolefins can suitably be those having a viscosity at 100° C. of from 2 to 20 centistokes as more fully described in U.S. Pat. No. 4,846,848 issued Jul. 11, 1989 to R. Miles et al., the description of which is incorporated herein by reference.

EXAMPLES

The following examples are presented to illustrate specific embodiments of the practice of this invention and should not be interpreted as limitations upon the scope of the invention.

Example 1

Epoxidation Of Ultravis 30™ Polyisobutylene

A two-liter, three-necked flask equipped with a mechanical stirrer and a heating mantle was charged with 687 grams of Ultravis 30™ polyisobutylene (mol. wt. 1300, 76% methylvinylidene, available from British Petroleum) and 550 ml of hexane. A mixture of 4.2 grams sodium acetate trihydrate and 150.5 grams 40% peracetic acid was added dropwise while maintaining the temperature between 35° C. and 45° C. The addition was complete in about one hour. The temperature was maintained for an additional 5 hours and the mixture was then allowed to cool overnight. The remaining acetic and peracetic acid mixture was siphoned off. Aqueous 5% sodium carbonate, 200 ml, was added cautiously to avoid excessive foaming. The mixture was transferred to a separatory funnel to remove the aqueous layer. The product was dried over anhydrous sodium sulfate, filtered, and solvent stripped to give 670 grams of product. Flash chromatography on Davison 62 silica gel indicated that the product was 85% epoxide and 15% unreacted polybutylene.

The partially converted epoxide, 442 grams in 500 ml hexane, was reacted further with a mixture of 48.5 grams of 40% peracetic acid and 1.4 grams of sodium acetate trihydrate at 45° C. for 16 hours. When isolated as above, 424 grams of 98+% epoxide product was obtained.

Example 2

Reaction Of Polyisobutylene Epoxide With Diethylenetriamine (DETA)

A one-liter, three-necked flask equipped with a mechanical stirrer and a heating mantle was charged with 380 grams polybutene epoxide prepared from Ultravis 30™ as in Example 1 and 180 grams diethylenetriamine. The mixture was heated at reflux (200° C.) under nitrogen for 20 hours. After cooling, the mixture was treated to remove unreacted DETA by dissolving the mixture in one liter of toluene and transferring the solution to a separatory funnel. After washing with two 300 ml portions of water, the toluene was stripped to give 370 grams of crude product containing 1.87% total nitrogen corresponding to 63% actives content. By "actives content" it is meant the content of the crude product, in weight percent, of the desired (or "active") product, i.e., the polyamine-polyolefin epoxide reaction product. Thus the remaining portion of the crude product is 37% by weight of unreacted polyolefin epoxide since the unreacted DETA was removed by washing. Thus the actives content is a measure of polyolefin epoxide conversion.

Example 3

Reaction Of Hydroxyalkyl-Substituted Polyamine Of Example 2 With Urea

A 500-ml flask was charged with 138 grams of hydroxyalkyl-substituted diethylentriamine prepared as in Example 2 and 3.7 grams of urea. The mixture was heated to 170° C. with stirring while purging the system with nitrogen for four hours. Vacuum was applied for 15 minutes to remove traces of dissolved ammonia. The product was then cooled under nitrogen. Analysis showed 1.83% total nitrogen and 0.71% basic nitrogen. Infrared spectroscopy showed a strong absorption at 1700 cm$^{-1}$ indicative of the cyclic urea. The product of 2 moles of the product of Example 2 with urea would have had an IR absorption at about 1643 cm$^{-1}$ but no absorption at 1643 cm$^{-1}$ was observed. A purified product was obtained by flash chromatography from silica gel, i.e., elution with hexane-diethyl ether (1:1) removed any unreacted epoxide or polybutene followed by elution with a mixture of hexane:diethyl ether:methanol:isopropylamine (8:8:3:1) to produce the purified product containing 2.92% total nitrogen and 1.10% basic nitrogen.

Example 4

Epoxidation Of Ultravis 10™ Polyisobutylene

Example 1 was repeated except Ultravis 10™ polyisobutylene (mol. wt. 950, 76% methylvinylidene, available from British Petroleum) was used in place of Ultravis 30™. Flash chromatography on Davison 62 silica gel indicated the product was 95% epoxide and 5% unreacted polybutylene.

Example 5

Reaction Of Polyisobutylene Epoxide With Diethylenetriamine (DETA)

Example 2 was repeated except using the polyisobutylene epoxide of Example 4. The product contained 2.49% total nitrogen corresponding to 63% actives.

Example 6

Reaction Of Hydroxyalkyl-Substituted Diethylenetriamine Of Example 5 With Urea

Example 3 was repeated using 370 grams of the hydroxyalkyl-substituted diethylenetriamine of Example 5 and 13.2 grams of urea. The crude product contained 2.45% total nitrogen and 0.83% basic nitrogen. Flash chromatography produced a purified product containing 3.49% total and 1.15% basic nitrogen.

Example 7

Reaction Of Polyisobutylene Epoxide With Di(1,3-propylene)triamine

Three hundred seventy-eight grams of polyisobutylene epoxide prepared as in Example 1 was reacted with 257 grams di(1,3-propylene)triamine at 200° C. for 18 hours under nitrogen. Work-up as in Example 2 gave 403 grams of crude product containing 1.94% total nitrogen corresponding to a 67% actives content.

Example 8

Reaction Of Hydroxyalkyl-Substituted Di(1,3-propylene)triamine Of Example 7 With Urea In a manner similar to Example 3, 395 grams of di(1,3-propylene)triamine adduct of polyisobutylene epoxide of Example 7 was reacted with 10.9 grams of urea. The product was worked-up in the same manner as Example 3. The crude product contained 2.85% total and 0.76% basic nitrogen. Flash chromatography produced a purified product containing 2.76% total and 1.03% basic nitrogen.

Intake Valve Deposit Control Evaluation

A series of tests were performed wherein the hydroxyalkyl-substituted, cyclic urea-substituted polyamines of Examples 3, 6 and 8 were blended in gasoline and their deposit control activity tested in an ASTM/CFR Single-Cylinder Engine Test.

In carrying out the tests, two different Waukesha CFR single-cylinder engines were used, labelled "12A" and "12B" in Table 1 below. The run is carried out for 15 hours, at the end of which time the intake valve is removed, washed with hexane and weighed. The previously determined weight of the clean valve is subtracted from the weight of the valve. The difference between the two weights is the weight of the deposit with a lesser amount of deposit measured connoting a superior additive. The operating conditions of the test are as follows: water jacket temperature 100° C. (212° F.); manifold vacuum of 12 in. Hg; intake mixture temperature 50.2° C. (125° F.); air-fuel ratio of 12; ignition spark timing of 40° BTC; engine speed is 1800 rpm; the crankcase oil is a commercial 30W oil. The amount of carbonaceous deposit in milligrams on the intake valves is measured and reported in the following Table 1.

The base fuel tested in the above test is a regular octane unleaded gasoline containing no fuel deposit control additive. The base fuel is admixed with the various additives at 200 ppma (parts per million of actives), along, in some cases, with 800 ppm Chevron 500R carrier oil. Also presented in Table 1 for comparison purposes are values for (i) a commercially available polybutylene amine deposit control additive and (ii) a commercially available polyether amine deposit control additive, each having recognized performance in the field.

Octane Requirement Increase (ORI)

A series of tests were run wherein the hydroxyalkyl-substituted, cyclic urea-substituted amines of Examples 3, 6 and 8 were blended in gasoline and their ORI determined in a CLR single cylinder engine test.

In carrying out the test, a laboratory engine test was used to evaluate the tendency of the additives to contribute to ORI. The test engine is a CLR single-cylinder, balanced, high-speed, four-cycle engine designed primarily for oil test and research work. It is manufactured by the Laboratory Equipment Corporation of Mooresville, Ind. The major engine dimensions are:

| Bore | 3.80 in. |
| Stroke | 3.75 in. |
| Displacement | 42.5 cu. in. |
| Compression Ratio | 8:1 |

The carburetor, intake manifold, and distributor were slightly modified to facilitate the test procedure. These modifications were made in order to make the engine's ORI characteristics comparable to modern-day automobiles. The test procedure involves engine operation for 90 hours (24 hours a day) on a prescribed load and speed schedule representative of typical vehicle driving conditions. ORI is the difference in fuel octane required for knock-free operation of the engine before and after 90 hours operation using the additized fuel.

The base fuel and amounts of additive are the same as for the intake valve test described above. The results are summarized in Table 1 below.

Referring to Table 1, a comparison of Examples 9 and 10 shows the addition of commercial polybutylene amine results in a significant reduction in SCITV deposits. There is an increase in ORI requirement using the CA1 compared to the ORI of the base gasoline.

A comparison of Examples 9 and 11 shows the addition of the more expensive commercial polyether amine results not only in a significant reduction in SCITV deposits but the ORI requirement increase is less for the CA2 additive than the CA1 additive and in one case (the 12C engine) appears better than the base gasoline (2.50RI using CA2 compared with 3.0 for base gasoline).

A comparison of Examples 12 and 13 with Examples 9 and 11 shows the addition of the additives of this invention (Examples 12 and 13) results in a significant decrease in SCITV deposits compared with the base gasoline (Example 9) especially when a carrier oil is used (Example 13 compared with Example 9). Very surprising are the ORI results for Example 12 which are about the same as the ORI results for the base gasoline (Example 9). A comparison of the ORI results of Example 12 with the commercial results in Examples 10 and 11 shows even better ORI than either of the commercial additives. The use of a carrier oil appears to improve the SCITV deposits (compare Example 13 with Example 12) but appears to increase, relatively, the ORI (compare 12D results for same two examples).

The results in Example 14 are especially interesting. The SCITV deposits in the 12B engine were very low on the order of the more expensive use of CA2 commercial additive (compare Example 14 with Examples 9, 10 and 11) plus the ORI increase was very low (equal to or better than the use of CA2).

The difference between the additives used in Examples 12 and 14 is the molecular weight of the polybutylene epoxide component. In Example 12, the polybutylene epoxide made from Ultravis 30™ had a molecular weight of about 1300 whereas the molecular weight of the Ultravis 10™ used for the additive of Example 14 was about 950.

Examples 15 and 16 show the use of a six-membered cyclic ether based additive results in lowered SCITV (compared with base gasoline, Example 9) deposits and comparatively good ORI.

The applicant's invention is not to be limited by the foregoing examples but only by the following claims.

TABLE 1

| EX. NO. | ADDITIVE | PPMA[6] | PPM 500R[7] | SCITV[1], mg 12A | 12B | ORI 12C ORI | CCD[5], g | 12D ORI | CCD[5], g |
|---|---|---|---|---|---|---|---|---|---|
| 9 | None | — | — | 168.8[4]; 188.4[4] | 212.3; 197.4 | 3.0 | 0.75 | 1.8 | 1.16 |
| 10 | CA1[2] | 200 | 800 | 11.6; 36.6 | 6.5; 28.6 | 5.3 | 2.35 | 5.2; 5.1 | 2.09; 2.27 |
| 11 | CA2[3] | 200 | — | 10.6, 3.2 | 1.0; 3.1 | 2.5; 2.5 | 1.26; 0.97 | 3.1; 3.1 | 1.39; 1.40 |
| 12 | From Ex. 3 | 200 | | 121.3; 91.4 | — — | — | — | 2.1; 2.7 | 1.16; 1.36 |
| 13 | From Ex. 3 | 200 | 800 | 50; 8.8; 25; 74 | — — | — | — | 4.5; 4.5 | 1.93; 1.90 |
| 14 | From Ex. 6 | 200 | | — — | 2.6; 0.1 | 3.4 | 1.27 | — | — |
| 15 | From Ex. 8 | 200 | | — — | 197.2; 103.9 | 3.5; 3.9 | 1.45; 1.42 | — | — |
| 16 | From Ex. 8 | 200 | 800 | — — | 109.1; 184.1 | — | — | — | — |

[1]SCITV = Single Cylinder Intake Valve.
[2]CA1 = Commercial Additive 1 (a polybutene amine).
[3]CA2 = Commercial Additive 2 (a polyether amine).
[4]More than one number indicates more than one test.
[5]CCD = Combustion Chamber Deposits.
[6]PPMA = Parts per million actives.
[7]500R = A mineral oil carrier oil available from Chevron U.S.A. Chevron Neutral Oil 500R is a highly refined base oil having a pour point of −12° C. (Max.) and a viscosity of 98.6 cSt at 40° C.

What is claimed is:

1. A cyclic urea having the formula:

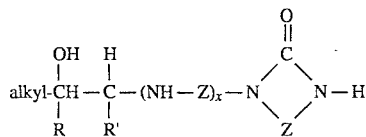

wherein the alkyl group has an average molecular weight from 400 to 5000, is branched with at least one branch per six carbon atoms along the chain;

R and R' can be the same or different and are selected from hydrogen and a lower alkyl group having 1 to 4 carbon atoms;

x is the integer 1 or 2; and

Z is the same or different and is selected from the group consisting of —$CH_2CH_2$—; —$CH_2CH_2CH_2$—; and

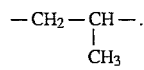

2. A cyclic urea in accordance with claim 1 wherein said alky group has a molecular weight from about 900 to 2500.

3. A cyclic urea in accordance with claim 1 where Z is selected from —$CH_2CH_2$— and

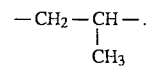

4. A cyclic urea in accordance to claim 1 prepared by the reaction of (i) a polyolefin epoxide having an average molecular weight of about 400 to 5000, wherein the polyolefin is branched with at least one branch per six carbon atoms along the chain (ii) a polyamine having from 3 to 4 amine nitrogen atoms and from 4 to about 9 carbon atoms and (iii) urea.

5. A cyclic urea in accordance with claim 4 wherein said polyolefin has a molecular weight from about 900 to 2500 and is branched with from 3 to 4 carbon atoms along the chain.

* * * * *